United States Patent
Robar et al.

(10) Patent No.: US 6,904,162 B2
(45) Date of Patent: *Jun. 7, 2005

(54) FILM PHANTOM FOR THREE-DIMENSIONAL DOSIMETRY

(75) Inventors: James Robar, Halifax (CA); Brenda Clark, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/698,461

(22) Filed: Nov. 3, 2003

(65) Prior Publication Data

US 2004/0120560 A1 Jun. 24, 2004

Related U.S. Application Data

(63) Continuation-in-part of application No. 09/436,917, filed on Nov. 9, 1999, now Pat. No. 6,668,073.
(60) Provisional application No. 60/108,281, filed on Nov. 12, 1998.

(51) Int. Cl.[7] .................................................. G06K 9/00
(52) U.S. Cl. ..................................................... 382/128
(58) Field of Search ........................ 250/336.1, 370.07, 250/251.1, 337, 580, 584–586; 382/128, 129, 130, 131, 132; 378/18, 64, 167, 204, 174, 207

(56) References Cited

U.S. PATENT DOCUMENTS

| | | | |
|---|---|---|---|
| 5,207,223 A | 5/1993 | Adler | 600/427 |
| 5,250,019 A | 10/1993 | McGinley | 600/1 |
| 5,339,347 A | 8/1994 | Slatkin et al. | 378/65 |
| 5,430,308 A * | 7/1995 | Feichtner et al. | 250/580 |
| 5,511,107 A * | 4/1996 | Sliski | 378/207 |
| 5,633,584 A | 5/1997 | Maryanskl et al. | 324/300 |
| 5,635,709 A | 6/1997 | Sliski et al. | 250/252.1 |
| 5,651,046 A * | 7/1997 | Floyd et al. | 378/207 |
| 5,661,310 A | 8/1997 | Jones | 250/584 |
| 6,668,073 B1 * | 12/2003 | Robar et al. | 382/128 |

* cited by examiner

*Primary Examiner*—Leo Boudreau
*Assistant Examiner*—Tom Y. Lu
(74) *Attorney, Agent, or Firm*—Oyen Wiggs Green & Mutala

(57) ABSTRACT

A method and system for recording and verifying three-dimensional dose distributions a film phantom uses a phantom which includes a cavity for receiving film sheets. A three-dimensional radiation dose described by a stereotactic radiosurgery plan can be delivered to the phantom while the cavity is loaded with film. The film can be developed to provide multiple dose images. Thereafter, based on the multiple dose images, a measured three-dimensional dose distribution map is obtained. The phantom may have a pattern of translucent areas which expose fiducial marks on the film. The fiducial marks may be used to determine a position and orientation of the film relative to the phantom.

24 Claims, 8 Drawing Sheets

FILM PHANTOM FOR THREE-DIMENSIONAL DOSIMETRY

CROSS-REFERENCE TO RELATED APPLICATION

This application is a continuation-in-part of application Ser. No. 09/436,917 filed on 9 Nov. 1999 now U.S. Pat. No. 6,668,073 and claims the benefit under 35 U.S.C. §119(e) of the filing date of U.S. application Ser. No. 60/108,281, filed Nov. 12, 1998.

TECHNICAL FIELD

This invention relates to methods and systems for recording and verifying three-dimensional dose distributions to be administered during radiotherapy. The invention has particular application in recording and verifying three-dimensional dose distributions to be administered during stereotactic radiosurgery.

BACKGROUND

Stereotactic radiosurgery is a method for treating brain lesions, using collimated convergent beams of x-ray photons produced by a clinical linear accelerator. In order to conform the administered dose distribution to the delineated volume of a lesion, while sparing healthy adjacent tissue, the method requires an extremely high spatial accuracy of approximately ±1 millimeter (mm). The method also requires an accuracy of ±2% in controlling the magnitude of the administered dose.

Because the success of stereotactic radiosurgery hinges on the accurate delivery of dosage of x-ray photons to the lesion, simulated radiosurgery using a suitable phantom, or a pseudo-object, is performed prior to actual application of the radiosurgery to a human patient, to record and verify the resulting dose distribution. The result of the simulated radiosurgery may be used to adjust stereotactic radiosurgery parameters to ensure that the desired dose distribution is applied to a human patient. Currently, ionization chambers, diodes, and diamond detectors are used to measure radiation dose distribution. (See, for example, U.S. Pat. No. 5,635,709.) Unfortunately, such devices provide a dose measurement at a single point at a time. Alternatively, radiosensitive polymer gels have been used as prototypical three-dimensional dosimeters as described, for example, in U.S. Pat. No. 5,633,584. Unfortunately, such gels are not well established, and require an expensive magnetic resonance imaging (MRI) scanner in order to read the recorded dose distribution.

SUMMARY OF THE INVENTION

One aspect of this invention provides a film phantom system for recording and verifying three-dimensional dose distributions. The film phantom system may be used, for example, to verify radiation doses in stereotactic radiosurgery. The film phantom system comprises a body of tissue-equivalent material. The body surrounds a cavity capable of receiving a stack of sheets of film separated by tissue-equivalent spacers. The cavity has walls which include at least one translucent area which extends through at least one opaque area of the walls. The at least one translucent area is configured to intersect edges of different sheets of film in a stack of sheets of film in the chamber at different locations. Light passing through the translucent area can expose fiducial marks on edges of sheets of film stacked within the cavity.

Another aspect of the invention provides a method of recording and verifying three-dimensional dose distributions. The method comprises providing a phantom including a tissue equivalent body surrounding a cavity; loading multiple layers of film separated by multiple spacers having tissue-equivalent characteristics into the cavity; delivering radiation to the body including the multiple layers of film; and, before, during or after delivering the radiation to the body, allowing light to pass through translucent areas in walls of the cavity to expose a pattern of fiducial marks on edges of the multiple layers of film. The pattern is different for each of the multiple layers of film. The method includes removing the multiple layers of film from the cavity; obtaining multiple dose images based on the multiple layers of film; and, using the patterns of fiducial marks exposed on the edges of the multiple layers of film to arrange the multiple dose images in sequence.

Further aspects of the invention and features of various embodiments of the invention are described below.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Stereotactic radiosurgery performed on patients in clinical settings typically involves the following steps (1) through (6), wherein each step introduces its own spatial uncertainty. The present invention provides a simulation method and system for recording and verifying three-dimensional dose distributions, which closely model the actual stereotactic radiosurgery, so as to quantify each of these uncertainties.

(1) A head ring (typically metal) is attached to encircle a patient's skull.

(2) A localizer box is attached to the head ring. The localizer box is a plastic box that clips securely onto the head ring and fits around the patient's head. On the faces of this box are marks, which are identifiable in CT images in order to establish a coordinate system in which the position of the patient's lesion is defined.

(3) The patient's head is imaged using a CT or MRI scanner.

(4) Based on the acquired images of the head and the lesion, an appropriate arrangement of the treatment beam is established using commercially available treatment-planning software.

(5) A target-positioner box replaces the localizer box on the head ring. The target-positioner box is similar to the localizer box, except that it is used to accurately position the patient on the linear accelerator couch used in stereotactic radiosurgery. Attached to the faces of the target-positioner box are marks, which are used for aligning the patient with fixed reference laser beams.

(6) The treatment is administered using a number of beams of x rays generated by the linear accelerator.

To accurately simulate actual stereotactic radiosurgery, as outlined above in steps (1) through (6), the method and system of the present invention have been developed for recording and verifying three-dimensional dose distributions using an anthropomorphic film phantom in a form completely compatible with all the clinically used equipment (head ring, localizer box, target-positioner box, various medical imaging scanners, etc.).

Figure 1:
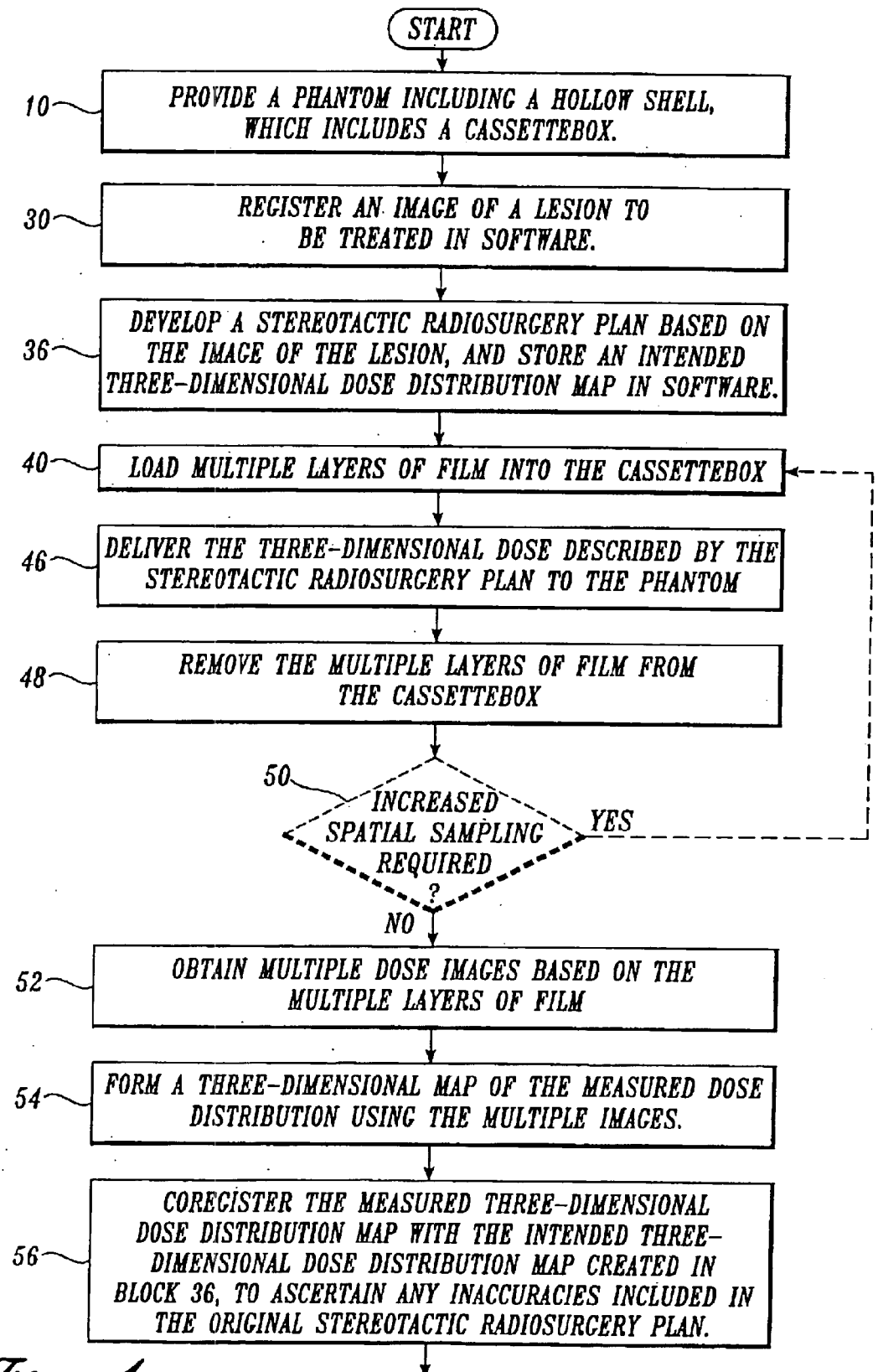
FIG. 1 is a flowchart of a method of recording and verifying three-dimensional dose distributions using a phantom in accordance with the present invention.
Figure 2:
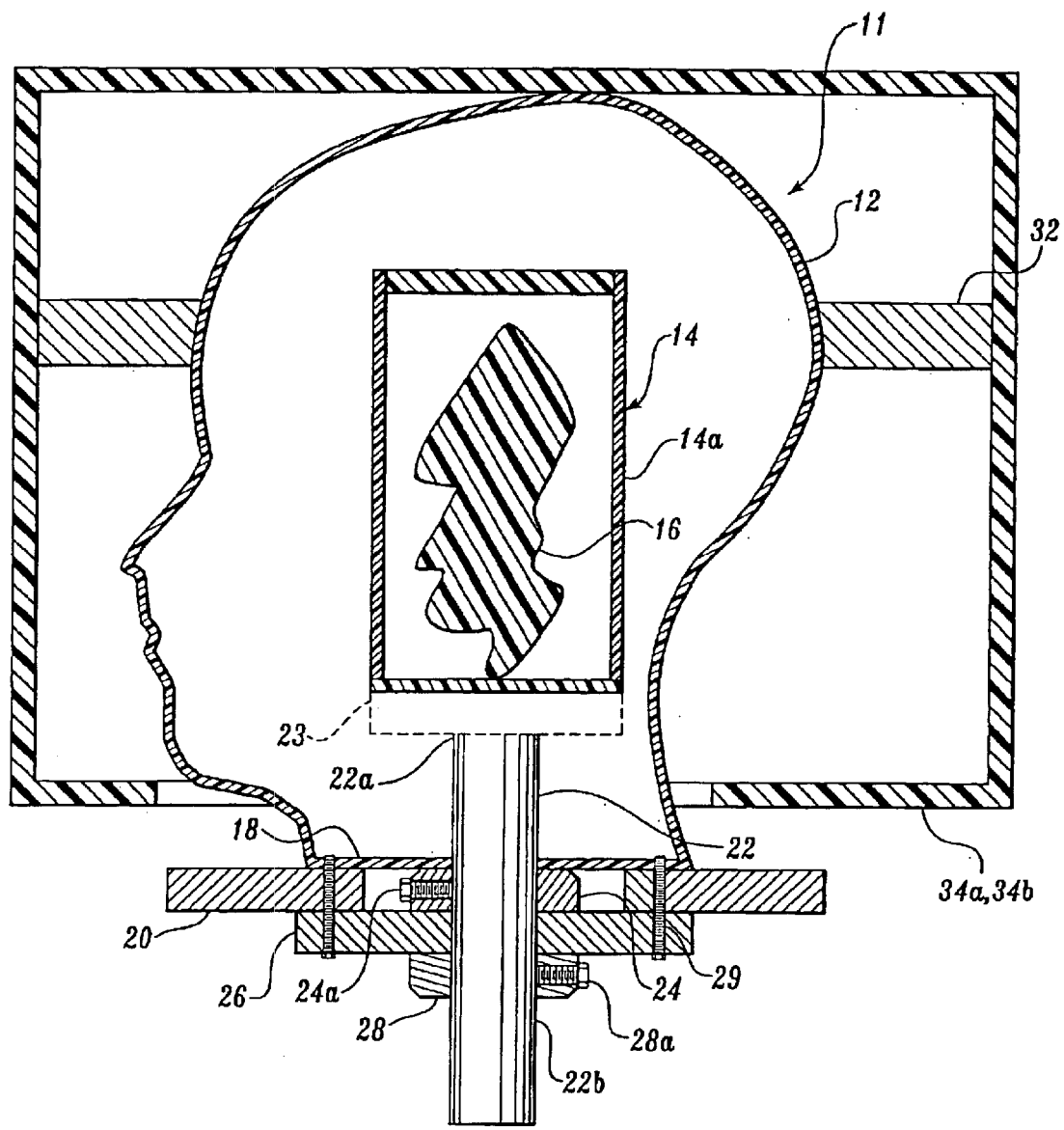
FIG. 2 is a cross-sectional view of a phantom including a head-shaped hollow shell and a box containing a simulated lesion, suitable for use in the present method.

Specifically, FIG. 1 is a flowchart illustrating the steps involved in the method of the present invention using a phantom. Referring additionally to FIG. 2, first, as indicated in box 10 of FIG. 1, a phantom 11 including a hollow shell 12 is provided, which houses a box or cassettebox 14.

The hollow shell 12 is configured so as to closely simulate a human head in terms of the head's treatment (i.e., how the head is supported, imaged, treated, etc.) throughout the entire process of stereotactic radiosurgery. Thus, as illustrated in FIG. 2, the hollow shell 12 is preferably in the shape of an average human head. While in the following description the hollow shell 12 is referred to as "head-shaped shell 12" for convenience, it is to be understood that the hollow shell 12 may take other shapes, for example, cylindrical, spherical or light-bulb shapes. The head-shaped shell 12 is made of plastic, for example, or any other suitable material that has tissue-equivalent characteristics. A neck 18 of the head-shaped shell 12 is open and is supported by a ring-shaped neck plate 20, which is in turn supported by a neck cover plate 26. In use, the head-shaped shell 12 is filled with material that simulates brain tissue, such as water. Water is considered tissue equivalent because it closely resembles tissue in terms of effective atomic number, density, and electron-density, which are all factors that affect absorption and attenuation of x rays.

Figure 3:
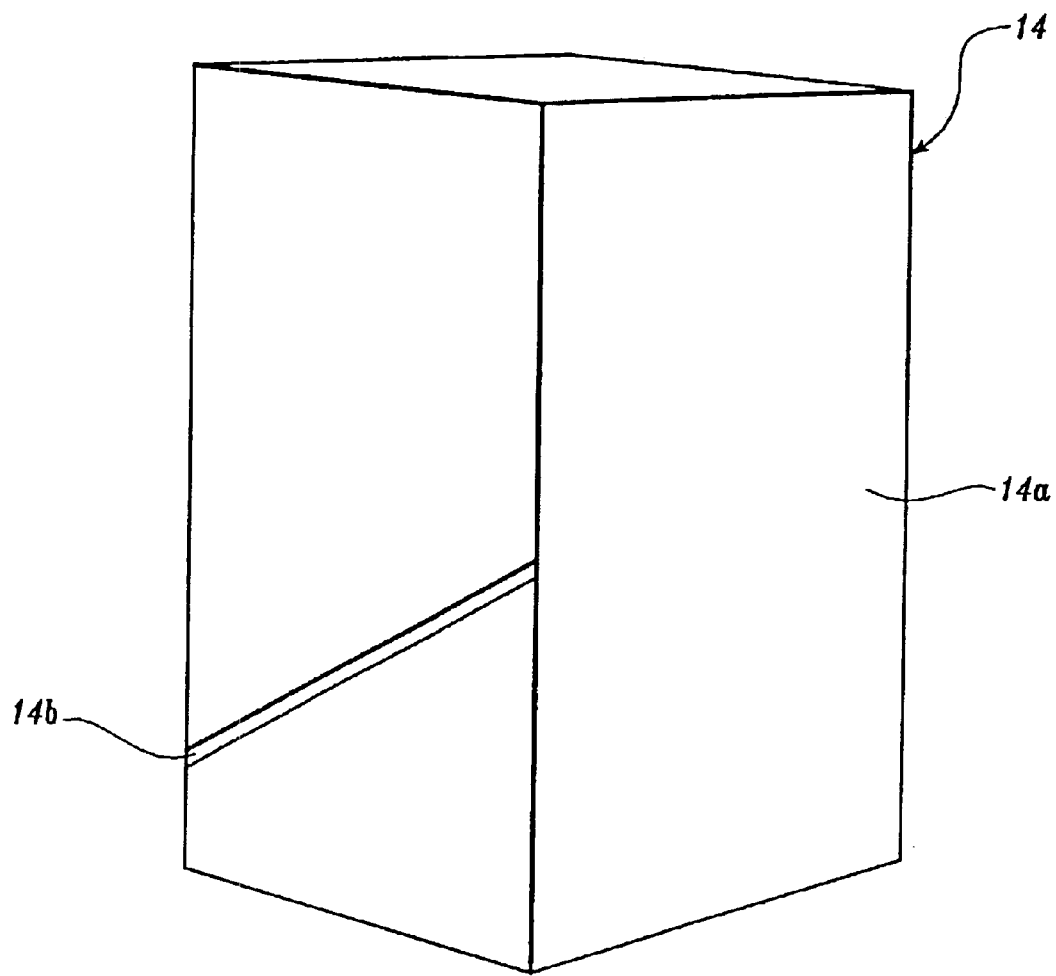
FIG. 3 is a perspective view of the box of FIG. 2.

The head-shaped shell 12 is adapted to adjustably position and mount the cassettebox 14. Referring additionally to FIG. 3, the cassettebox 14 is made of suitable material having tissue-equivalent characteristics, for example, plastic such as polystyrene, Solid Water® available from Gammex, Inc. of Wisconsin, USA; Plastic Water® available from Computerized Imaging Reference Systems, Inc. of Virginia, USA; and Lucite® available from E.I. Du Pont de Nemours & Co. of Delaware, USA. Preferably, the cassettebox 14 is made of opaque material, or outer walls 14a of the cassettebox 14 are covered with a tissue-equivalent coating or veneer that is opaque to visible light, except for a diagonal strip 14b provided on one wall of the cassettebox 14. The strip 14b is also made of tissue-equivalent material, such as translucent polystyrene. Construction of the cassettebox 14 as illustrated in FIG. 3 is advantageous for indexing each of multiple layers of radiographic film loaded in the cassettebox, as more fully described below.

Returning to FIG. 2, the cassettebox 14 is inserted through the open neck 18 of the head-shaped shell 12 and is adjustably positioned therein. To this end, the cassettebox 14 is supported on one end 22a of a rod 22 via an attachment mechanism 23. Any mechanism that securely attaches the rod end 22a to the cassettebox 14 may be used. For example, the rod end 22a may be threaded, bolted, or adhered to the cassettebox 14. The other end 22b of the rod 22 passes through a first bushing 24, the neck cover plate 26, and a second bushing 28, which all include centrally located apertures to allow insertion of the rod 22 therethrough. The first and second bushings 24, 28 include first and second set screws 24a, 28a, respectively. Thus constructed, the position of the cassettebox 14 can be freely adjusted vertically within the head-shaped shell 12 by sliding the rod 22 along its longitudinal axis, and the position of the cassettebox 14 can be secured at a preferred location by using the set screws 24a, 28a to tighten the first and second bushings 24, 28. It is also noted that by axially rotating the rod 22, the angular orientation of the cassettebox 14 with respect to the head-shaped shell 12 can also be adjusted throughout the 360° range. To accurately adjust the angular orientation of the cassettebox 14, the neck cover plate 26 may have angular gauge indicia, as on a protractor.

The head-shaped shell 12, the neck plate 20, and the neck cover plate 26 are assembled together using any suitable means, such as one or more bolts 29. By assembling and disassembling these components, the cassettebox 14 can be freely inserted into and removed from the head-shaped shell 12.

Alternatively, or additionally, to the vertical and angular adjustment of the cassettebox 14 with respect to the head-shaped shell 12 as described above, the cassettebox 14 may be adapted to allow for other types of adjustment. For example, the attachment mechanism 23 may include a slotted arm extending generally perpendicularly from the rod end 22a to couple the cassettebox 14 to the rod 22 so that the cassettebox 14 can be adjustably positioned off the longitudinal axis of the rod 22. As a further example, the attachment mechanism 23 may include a plastic universal ball-joint to couple the cassettebox 14 and the rod end 22a together so that the cassettebox 14 can be freely rotated or tilted with respect to the rod 22. Various other types of attachment mechanisms 23 for positioning the cassettebox 14 at any desired location inside the volume of the head-shaped shell 12 may be used.

Next, as indicated in block 30 of FIG. 1, an image of a lesion to be treated, including the lesion's relative position with respect to the head-shaped shell 12, is registered in treatment-planning software. Any commercially available treatment-planning software may be used, such as Brain-SCAN® available from BrainLAB Medical Computersysteme GmbH of Germany and XPlan® available from Radionics, Inc. of Massachusetts, USA. Various methods may be used to register the image of a lesion in the software. For example, an image or three-dimensional contour of the actual lesion in a patient may be transferred to the software, as routinely done in the art.

Alternatively, a simulated lesion 16 (see FIG. 2) that models the actual lesion to be treated may be prepared. The simulated lesion 16 is made of material that is visible in CT and MRI images, for example, plastic or wax. By molding plastic or wax, one may freely form a lesion of various sizes and shapes to simulate a variety of actual lesions encountered in clinical settings. The simulated lesion 16 is then securely positioned within the cassettebox 14 using any suitable means (for example, providing a small pin that passes into both the cassettebox 14 and the simulated lesion 16). The rest of the cassettebox 14 is filled with tissue-equivalent material such as water. Thereafter, the cassettebox 14 is secured at a predetermined position within the head-shaped shell 12, so that the simulated lesion 16 will occupy the same position with respect to the head-shaped shell 12 as the position that the actual lesion occupies with respect to the actual human head. Next, an image of the head-shaped shell 12 including the cassettebox 14 containing the simulated lesion 16 is taken, using, for example, a CT or MRI scanner. The image of the simulated lesion 16 is then transferred to the treatment-planning software.

The method of taking a CT or MRI image is well known in the art and, thus, is not described in detail here. It is to be noted, however, that the head-shaped shell 12 is advantageously supported by a head ring 32 and an outer localizer box 34a when the image of the simulated lesion 16 is taken. The head ring 32 is a common clinical device used to encircle and support a human skull when the head needs to undergo certain scanning or radiosurgical operations. Since the head-shaped shell 12 is modelled after an average human head, the head ring 32 may be used to support the head-shaped shell 12 to simulate actual image taking. The head ring 32 is typically attached to the phantom 14 using a plurality of carbon fiber or metallic pins. The localizer box 34a, typically, is also a commonly used clinical component that is adapted to be coupled to the head ring 32 to accurately position a human head (or a head-shaped shell in the present case). The localizer box 34a includes marks thereon that are used during the imaging of the head-shaped shell 12 as reference points in order to accurately define the location of the simulated lesion 16. Once the image of the simulated lesion 16 is taken, the cassettebox 14 is removed from the head-shaped shell 12 and the simulated lesion 16 is removed from the cassettebox 14. Also, the localizer box 34a is removed from the head ring 32.

Next, as indicated in block 36 of FIG. 1, a stereotactic radiosurgery plan, including an intended three-dimensional dose distribution map, is developed in the treatment-planning software based on the registered image of the lesion. The intended dose distribution map developed is registered in the treatment-planning software. The method of creating and registering a three-dimensional dose distribution map is well known in the art and, thus, is not described in the present application.

Then, as indicated in block 40 of FIG. 1, multiple layers of radiation-sensitive film 42, for example, radiographic film or radio chromic film, are loaded into the cassettebox 14. See FIG. 4 additionally. Each film (typically approximately 0.2 mm thick) is separated from each adjacent film by a spacer 44 having tissue-equivalent characteristics, such as any suitable plastic including polystyrene, Solid Water®, Plastic Water®, and Lucite®. The film 42 and the spacers 44 are layered together without leaving an air gap therebetween, so that the assembly of the film and the spacers will have tissue-equivalent characteristics. The thickness of the spacer 44 is to be determined based on various factors. To increase spatial resolution, more sheets of the film 42 should be used, and the thickness of the spacers 44 should be decreased accordingly so that all the film can be loaded into the cassettebox 14 having a given volume. At the same time, however, the number of sheets of the film 42 should not be exorbitant, so that the time required for processing all the film will not be excessive. Typically, commercially available polystyrene sheets have a thickness of approximately 1/8" (3.2 mm). This thickness has been found to be adequate for the spacers 44 to meet all the requirements as described above, to be suitable for use in the present invention.

It is noted that any radiation-sensitive film suitable for recording dose distribution may be used. Radiographic film, such as Kodak X-Omat V film, may be advantageous in some situations because it is readily available in all radiation oncology centers, is affordable, and records the given dose with extremely high spatial resolution in two dimensions in the plane of the film. In other situations, radio chromic film may be used instead. Radiochromic film includes one or more microcrystalline monomeric layers that polymerize in response to exposure by radiation and, thus, unlike radiographic film, does not require chemical processing.

Once loaded with the film 42 and the spacers 44, the cassettebox 14 is inserted into the head-shaped shell 12 and securely positioned therein. The cassettebox 14 is positioned at the same location where the cassettebox 14 containing the simulated lesion 16 was previously situated with respect to the head-shaped shell 12, or where an actual lesion was situated with respect to a human head.

Next, as indicated in block 46 of FIG. 1, the three-dimensional radiation dose is delivered as described by the stereotactic radiosurgery plan (developed in block 36) to the head-shaped shell 12. At this time, the head-shaped shell 12, including the cassettebox 14 containing the film 42, is supported by the head ring 32, and by an outer target-positioner box 34b attached to the head ring 32. The target-positioner box 34b and the localizer box 34a take similar outer forms and, thus, both boxes 34a, 34b are represented by a single box illustrated in FIG. 2. The target-positioner box 34b, similarly to the localizer box 34a described above, is a known piece of equipment that is routinely used in stereotactic radiosurgery. Specifically, a paper printout of marks generated based on the intended three-dimensional dose distribution map is accurately positioned on the target-positioner box 34b. The target-positioner box 34b thus permits the alignment of the lesion with the isocenter (i.e., focus) of the linear accelerator used in stereotactic radiosurgery.

It is to be noted that different sizes of the film 42 can be included in the cassettebox 14 depending on each application, as long as the film is loaded into a cassettebox having the inner dimensions that closely match the particular film size to eliminate any air gaps. For example, relatively large sheets of film (12.0 cm×7 cm, for example) may be used to record relatively large radio surgical dose distributions, which are also large enough to be fed into typical automatic film processors, as more fully described below. Alternatively, relatively small sheets of film (6 cm×6 cm, for example) may be used, which are still large enough to record typical radiation dose distributions but may need to be attached to film leaders to be fed into conventional automatic processors.

Figure 4:
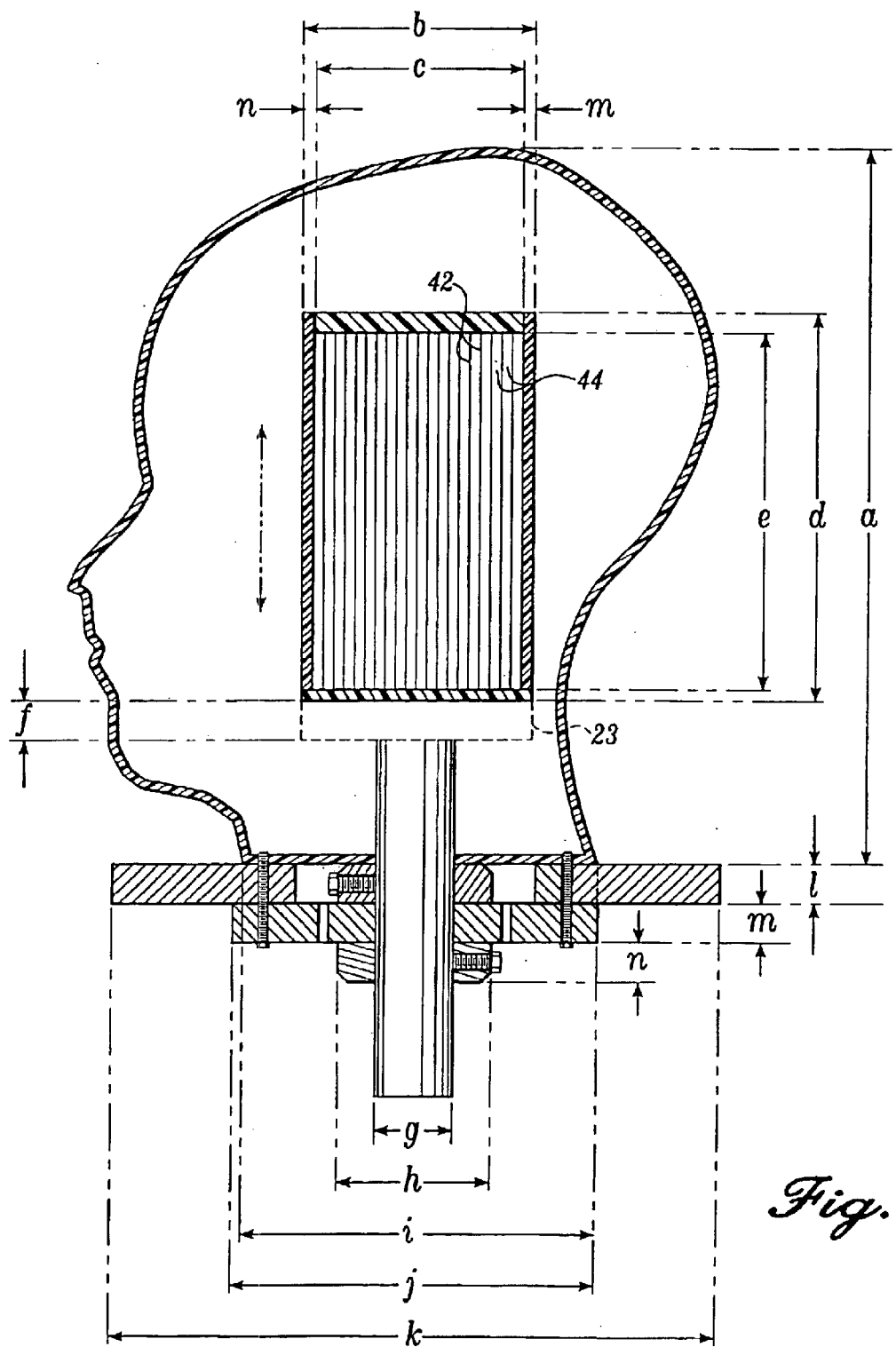
FIG. 4 is a cross-sectional view of the head-shaped hollow shell and the box of FIG. 2, containing multiple layers of film instead of the simulated lesion.

In FIG. 4, dimensions of the head-shaped shell 12, the cassettebox 14, the rod 22, and other parts described above are indicated as "a" through "n". It has been found that in one embodiment of the present invention adapted to accommodate film sized 12.0 cm×7 cm, the inner dimensions of the cassettebox 14 can be 7 cm×7 cm×12 cm, and the dimensions can be a=24.37, b=7.64, c=7.00, d=12.95, e=12.00, f=1.27, g=2.54, h=5.00, I=11.76, j=12.00, k=20.00, I=1.27, m=1.27, and n=1.27, respectively, all in centimeters (cm). In another embodiment adapted to accommodate film sized 6 cm×6 cm, the inner dimensions of the cassettebox may be 6 cm×6 cm×6 cm, and the dimensions "b" through "e" may be changed from above to b=6.64, c=6.00, d=6.95, and e=6.00, respectively, all in centimeters. These latter dimensions may be appropriate when radio chromic film is used, since this film is typically supplied with dimensions of 12.7 cm×12.5 cm and, thus, four sheets of film of roughly 6 cm×6 cm can be cut from one sheet of radio chromic film.

It should be understood, though, that the dimensions may be readily modified according to a specific application of the present invention, and are not limited to the specific examples given above. For example, the dimensions of the cassettebox 14 may be freely modified according to the maximum size of the dose distribution to be measured or the maximum size of the film to be used. Further, multiple cassetteboxes of different sizes may be provided, and used interchangeably depending on the particular needs of each application.

After the three-dimensional radiation dose is delivered to the film phantom, next, as indicated in box 48 of FIG. 1, the film 42 is removed from the cassettebox 14.

Figure 5C:
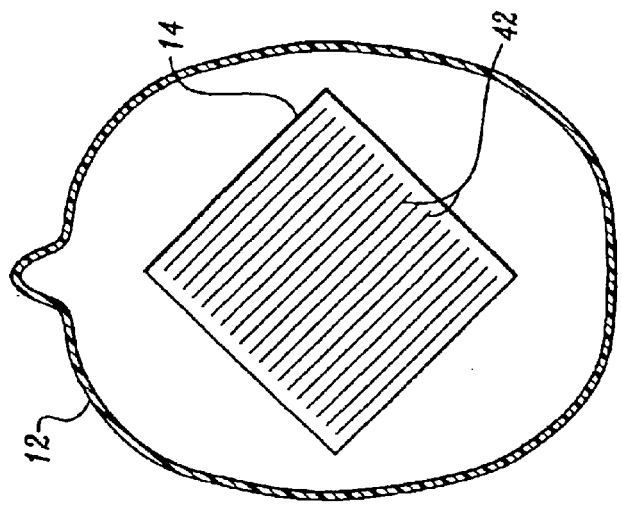
FIGS. 5A, 5B, and 5C are corresponding schematic top views of a head-shaped hollow shell including a box containing multiple layers of film, wherein the angular orientation of the box with respect to the head-shaped hollow shell is varied.
Figure 5B:
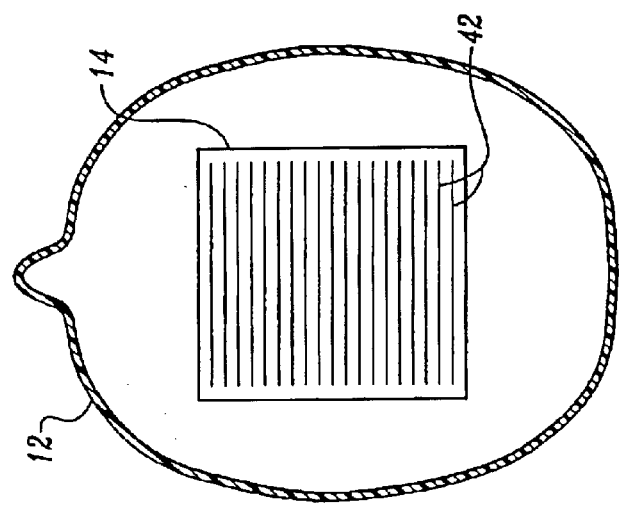
Figure 5A:
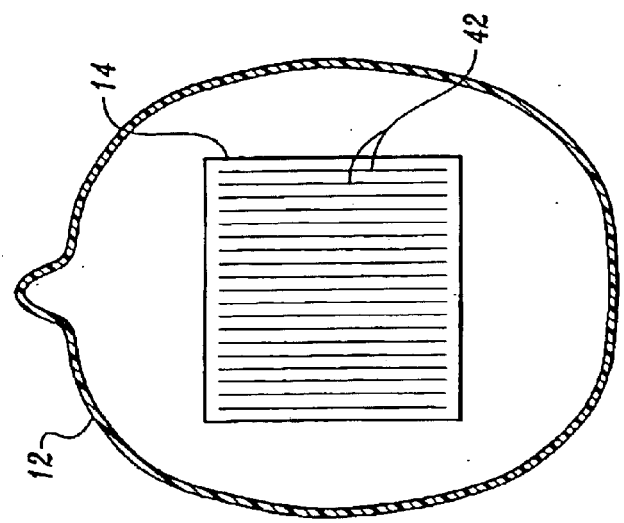

As indicated in box 50 of FIG. 1, optionally, it is determined if increased spatial sampling is required in order to improve the spatial resolution of the final three-dimensional dose distribution map. If so, the method returns to box 40, and repeats the steps of blocks 46 and 48 by varying the angular orientation of the cassettebox 14 with respect to the head-shaped shell 12. The loop may be repeated for a suitable number of times, by each time varying the angular orientation of the cassettebox 14. For example, in FIG. 5A, the dose distribution is first recorded with the film 42 plane along saggital planes. Then, in FIG. 5B, the cassettebox 14 is rotated 90 degrees from FIG. 5A, reloaded with unexposed film, and the dose distribution is recorded along coronal planes. Thereafter, in FIG. 5C, the cassettebox 14 is reloaded with another set of film and rotated to position the film planes at 45 degrees between the coronal and saggital planes. Plural sets of multiple layers of film 42 can then be used to obtain plural sets of multiple images of dosage later, which can be combined to improve spatial resolution of the final measured three-dimensional dose distribution map. When plural sets of multiple images are taken, the resolution is ultimately limited only by the resolution achievable in scanning the film (approximately 0.05 mm).

Thereafter, as indicated in box 52 of FIG. 1, multiple dose images can be obtained based on the multiple layers of film 42. Specifically, the layers of film 42 are processed using a standard film processor, as well known in the art. A film processor uses chemicals to perform the development, fixing, washing, and drying of the latent image recorded on the film 42. (The chemical processing step is not required if radio chromic film is used.) Next, the film 42 is digitized to form multiple images of the optical density pattern recorded on the film, using any suitable optical densitometer or scanner, also as well known in the art. Thereafter, using any suitable image processing software, the digitized optical density images are converted to images reflecting the dose administered at the location of each layer of the film 42 based on the sensitometric curve for the film 42, as well known in the art.

For the multiple dose images thus obtained to be later combined to form a three-dimensional dose distribution map, as described below, they need to be properly oriented and ordered. Orienting and ordering are preferably done automatically in the image processing software. To this end, it is advantageous to construct the cassettebox 14 or the outer wall 14a of the cassettebox 14 with material opaque to visible light except for a diagonal strip 14b on one face of the box 14, as illustrated in FIG. 3. Multiple layers of radiographic film are then loaded into the cassettebox 14 so that the planes of the film are perpendicular to the face containing the diagonal strip 14b. Because radiographic film is sensitive to visible light, this arrangement will expose small indexing marks on the edges of the film in the cassettebox 14. This allows for each film to have a uniquely located indexing mark. Determining the location of these exposed indexing marks (specifically, the distance of each mark from the bottom edge of the film) will provide means for automatically orienting and ordering the multiple layers of film and, hence, the multiple dose images developed therefrom. The capacity to automatically orient and order the radiographic film improves the ease of use of the phantom system of the present invention, by eliminating the need to maintain the order of the film during the unloading of the cassettebox and processing of the film.

Next, as indicated in block 54 of FIG. 1, the multiple dose images are combined to form a three-dimensional map of the measured (i.e., actual) dose distributions in the image processing software.

At this time, the multiple dose images may preferably be interpolated therebetween to generate a series of CT-format dose images at an arbitrary spatial frequency, which may be greater than the spatial frequency of the multiple dose images themselves. In other words, a series of CT-format dose images may be obtained to resample the measured dose distributions throughout the entire volume of the multiple layers of film 42. The CT-format dose images can then be transferred to the treatment-planning software, as described above with respect to block 36.

Finally, in block 56 of FIG. 1, the measured three-dimensional dose distribution map obtained in block 54 is spatially coregistered in the treatment-planning software with the intended three-dimensional dose distribution map that was created and registered into the software in block 36. When spatially coregistered, the two dose distribution maps share the same spatial scale, spatial location, and spatial orientation. This permits direct comparison between the measured and intended three-dimensional dose distribution maps.

Based on the coregistration, any inaccuracies included in the intended three-dimensional dose distribution map and, hence, the original stereotactic radiosurgery plan developed in block 36 can be ascertained, prior to the plan's actual application to a patient. Specifically, any discrepancies between the intended and measured dose distributions will reveal inaccuracies inherent in the lesion localization process and the subsequent treatment process. The stereotactic radiosurgery plan can then be adjusted to correct for these inherent inaccuracies.

As briefly noted at the beginning of the present description, the present invention also offers a phantom system for executing the method of the present invention described above. The system comprises a phantom including a hollow shell made of and filled with tissue-equivalent material, a cassettebox adjustably securable within the hollow shell, and multiple layers of film separated by tissue-equivalent spacers, which are removably loaded in the cassettebox. All of these components have been described in detail above.

Clinically, lesions may occur at various locations inside the brain. For example, acoustic neuromas occur near the ear, while nasopharyngeal carcinomas occur at the level of the neck. The design of the anthropomorphic phantom of the present invention permits the multiple layers of film (and the simulated lesion, if one is used) to be positioned anywhere within the hollow shell.

It is noted that many of the steps included in the present simulation method for localizing and treating a lesion as performed on the anthropomorphic film phantom are identical to those performed clinically in localizing and treating an actual lesion. Specifically, the invention may take the image of a simulated lesion while framing the hollow shell containing the lesion with a head ring and a localizer box, and subsequently radio surgically "treats" the lesion while framing the hollow shell with a head ring and a target-positioner box. The head ring and localizer/target-positioner boxes are equipment widely used in clinical settings. Accordingly, any systematic inaccuracies identified in the present method will also occur in the course of performing stereotactic radiosurgery on a patient. Such inaccuracies may be introduced in the processes of:

(1) localizing (imaging) the lesion;
(2) treatment-planning calculations of intended dose distributions;
(3) setting up of the patient on the linear accelerator couch used in radiosurgery;
(4) aligning of the target positioner box with the isocenter of the linear accelerator; and/or
(5) administering the radiation to the volume of the lesion using the linear accelerator.

Because the method of the present invention encompasses all errors associated with actual localization and treatment of a lesion, the invention provides complete and accurate simulations, which can be reliably used to optimize a stereotactic radiosurgery plan for a clinical application.

The present invention can be used for verification of conventional radiosurgery using circular beams, static conformal radiosurgery using multiple irregular collimators, and static or dynamic radiosurgery using a micromultileaf collimator. Because the system and method of the present invention are completely independent of the method of administering the radiation, they will remain applicable as radiosurgical technology advances.

Figure 6:
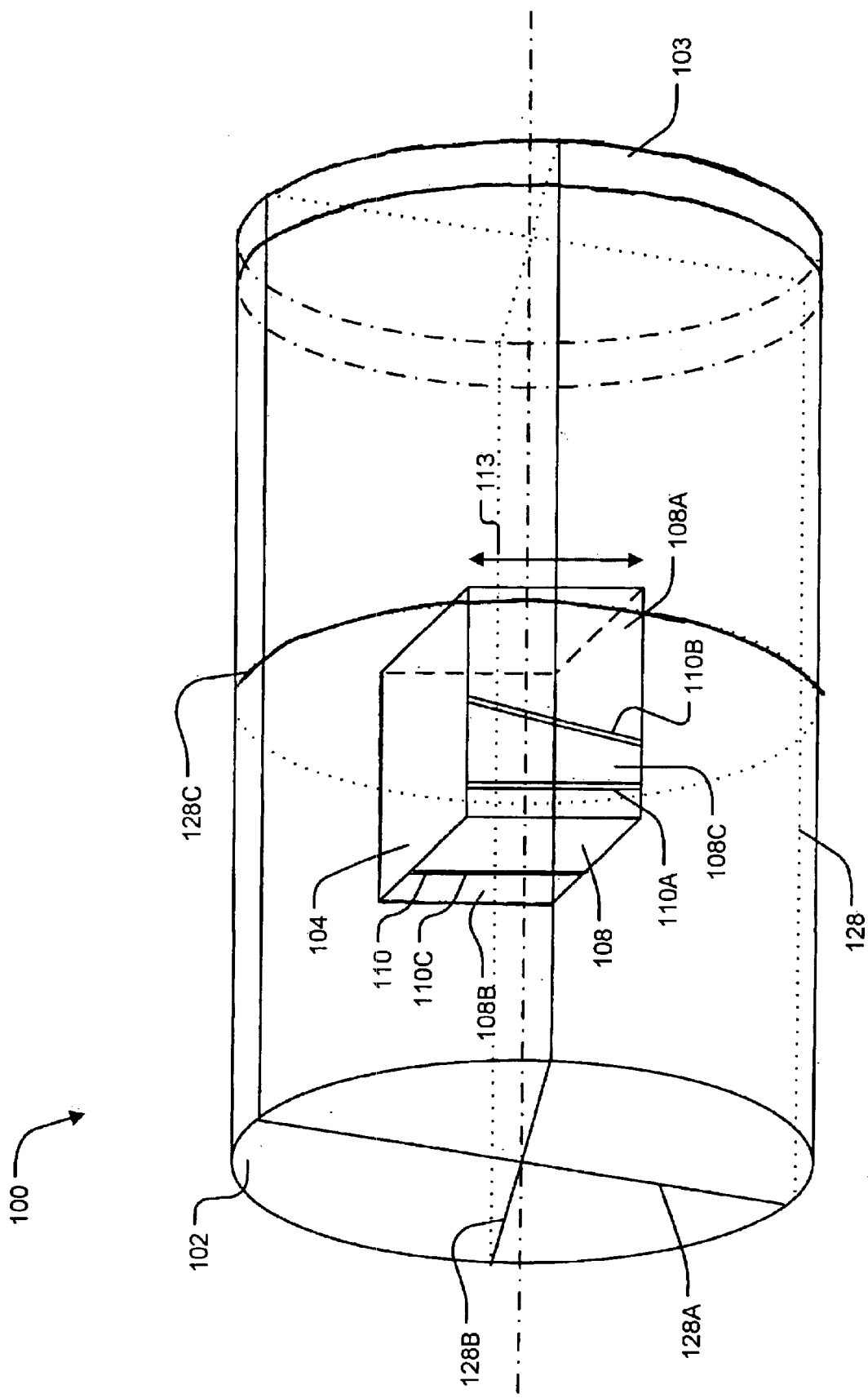
FIG. 6 is a partially schematic view of a film phantom according to an alternative embodiment of the invention.

FIG. 6 shows a phantom 100 according to an alternative embodiment of the invention. Phantom 100 comprises a body 102 of tissue-equivalent material having dimensions approximating those of a part of a body to be treated. In the illustrated embodiment, body 102 is cylindrical and approximates the size of a human head. Body 102 could optionally be more anatomically correct than the illustrated cylinder. In the further alternative, body 102 and could have other shapes that approximate the configuration of a body part.

A chamber 104 is located within body 102 at a location in which it is desired to measure a dose distribution to be produced by a linear accelerator or other source of radiation. Chamber 104 can receive sheets of film (not shown in FIG. 6) which may be separated by tissue-equivalent spacers 44, as described above with respect to FIGS. 1 and 4. Chamber 104 may be formed within a box which is removable from the rest of body 102 or may be formed directly in body 102. In the embodiment of FIG. 6, body 102 includes a lid 103 which can be removed to provide access to chamber 104.

In the embodiment of FIG. 6, the walls 108 of chamber 104 have a number of translucent strips 110 which pass through sections of the walls which are opaque to light. Preferably walls 108 of chamber 104 are opaque to light except for strips 110. Sheets of film 111 (see FIG. 7A) can be loaded into chamber 104 so that strips 110 extend across the edges of the sheets of film. Light passing through translucent strips 110 exposes small areas at the edges of the sheets of film to create fiducial marks. The fiducial marks can be used to determine the orientations and order of the sheets of film after processing. The fiducial marks can also be used to determine the position of each film sheet 111 relative to phantom 100.

Figure 7A:
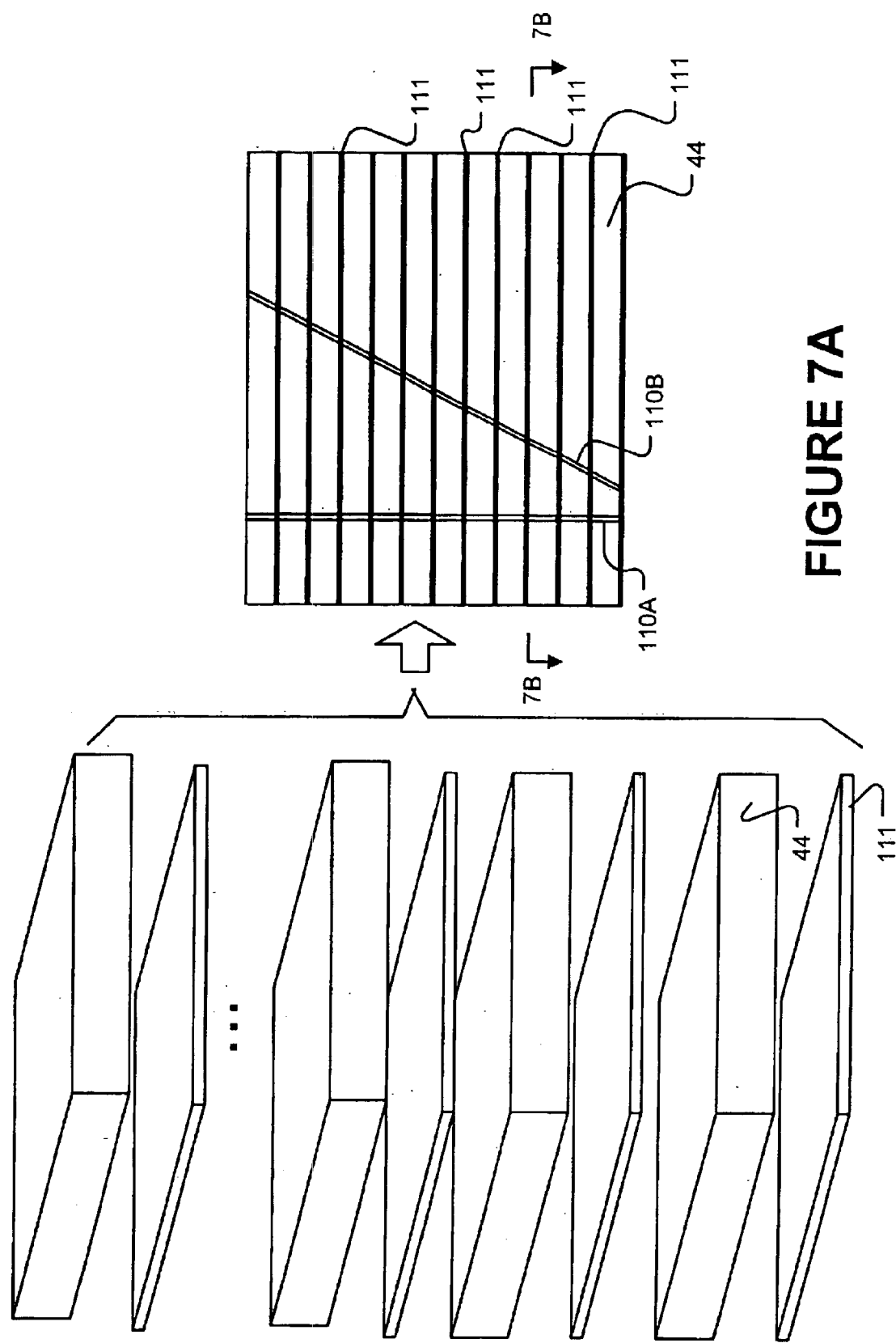
FIG. 7A is a schematic elevational view illustrating how fiducial marks can be exposed on edges of a stack of film sheets separated by spacers; and, FIG. 7B is a schematic cross sectional view through the stack of FIG. 7A showing one sheet of film bearing fiducial marks.
Figure 7B:
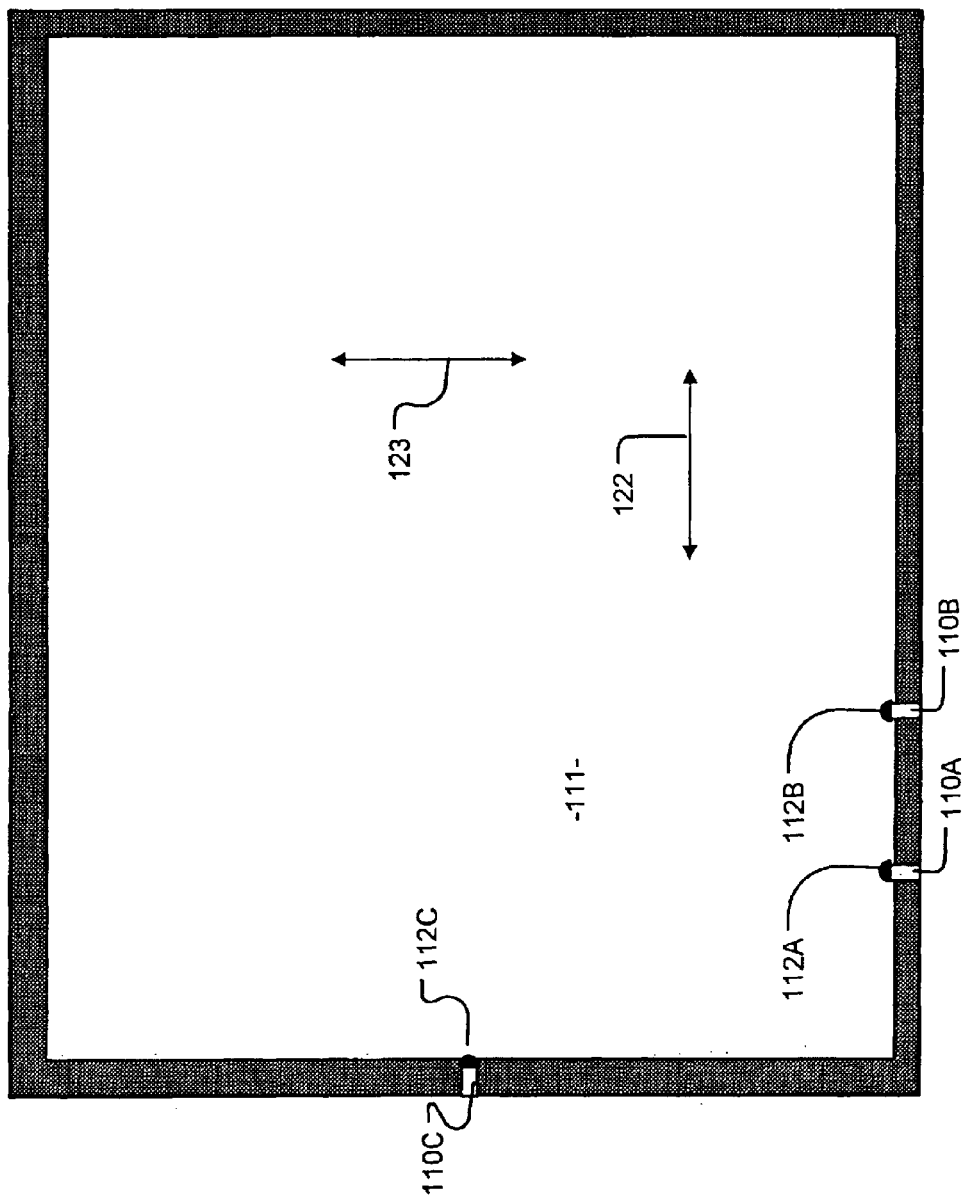

In the illustrated embodiment, one face 108A of chamber 104 has two translucent strips 110A and 110B. Translucent strips 110A and 110B are spaced apart from one another in a manner that varies with position along face 108A of chamber 104 on which translucent strips 110A and 110B extend. FIGS. 7A and 7B illustrate schematically how translucent strips 110A and 110B expose corresponding fiducial marks 112A and 112B (collectively fiducial marks 112) on the edges of film sheets 111. The distance D between fiducial marks 112 on a particular sheet of film is a function of the position of that sheet of film in direction 113.

The distance between translucent strips 110A and 110B varies with displacement in direction 113. Since film sheets 111 cross translucent strips 110A and 110B at different locations spaced apart in direction 113, fiducial marks 112 created on each sheet of film by light passing through translucent strips 110A and 110B have a spacing different from the spacing between fiducial marks 112 on other sheets of film. The spacing is a known function of position in direction 113. Even if the sheets of film become mixed up during processing, the spacing between fiducial marks 112 can be used to determine the order in which film sheets 111 were stacked in chamber 104, and the position of each sheet of film within chamber 104 in direction 113.

In preferred embodiments, the spacing between translucent strips 110A and 110B increases (or decreases) monotonically with displacement in direction 113. In the illustrated embodiment, translucent strips 110A and 110B are linear. Translucent strip 110A is parallel to the sides of wall 108A of chamber 104 and translucent strip 110B extends at an angle to translucent strip 110B. The distance between translucent strips 110A and 110B varies linearly with displacement in direction 113.

In the example embodiment illustrated in FIG. 6, translucent strips 110A and 110B create fiducial marks 112A and 112B on each sheet 111 of film that are spaced apart from one another along the edge of the film by a distance D, where D is given by:

$$D = D_0 + x \tan \theta \qquad (1)$$

where $D_0$ is the distance between translucent strips 110A and 110B at their closest point, x is the distance from the closest point to the sheet of film in direction 113 and $\theta$ is the angle between translucent strips 110A and 110B. Since $\theta$ and $D_0$ are known, x can be determined for each sheet 111 of film from the distance D between fiducial marks 112A and 112B on that sheet of film. The sequence of values of x indicates the order in which the sheets of film were stacked in chamber 104 during exposure. The values of x indicate the actual positions of sheets 111 in direction 113 relative to phantom 100.

In the illustrated embodiment, a second side 108B of chamber 104 is adjacent to side 108A. A translucent strip 110C extends along side 108B in a direction which crosses film sheets 111 stacked within chamber 104. Light passing through translucent strip 110C creates a third fiducial mark 112C on each sheet 111. Fiducial marks 112 can be used to determine the proper orientation of each film sheet 111 after processing.

As an alternative to providing a third strip 110C, strips 110A and 110B may be located in positions such that the fiducial marks 112A and 112B corresponding to translucent strips 110A and 110B themselves unambiguously determine the orientation of the film. For example, if translucent strip 110A is located to create fiducial marks a first distance from one edge of the film sheets and translucent strip 110B is routed so that it can never create a fiducial mark the first distance from an opposing edge of any of the film sheets then the correct orientation of any of the film sheets may be determined by observing the fiducial marks created by strips 110A and 110B.

Ideally, film sheets 111 fit exactly within chamber 104. However, in some cases film sheets 111 may be slightly undersized. This may result from imperfect cutting of the film sheets. Where film sheets 111 are undersized they may be free to move slightly within chamber 104. Therefore, their positions relative to the inner walls of chamber 104 are not perfectly known. Fiducial marks 112A and 112C can be used to compensate for any uncertainty regarding the positions of film sheets 111 in the plane of the film sheets.

Since translucent strips 110A and 110C fixed relative to the walls of chamber 104, light passing through these translucent strips produce corresponding fiducial marks 112A and 112C which are fixed relative to the walls of chamber 104. By measuring the positions of exposed features on film sheets 111 relative to fiducial marks 112A and 112C (as opposed to relative to the edges of film sheets 111), one avoids positional inaccuracies resulting from the film sheets shifting slightly side-to-side (as indicated in FIG. 7B by arrow 122) or lengthwise (as indicated in FIG. 7B by arrow 123) within chamber 104. In the illustrated embodiment, translucent strips 110A and 110C each extend substantially perpendicular to the planes of film sheets 111 (which lie parallel to base 108C of chamber 104).

There are many possible ways to provide translucent strips 110 or other structures for creating patterns of fiducial markings on film sheets 111. A suitable pattern of opaque and translucent areas may be provided in the walls of a removable box. The box may be constructed substantially as described above with respect to the embodiments of FIGS. 1 to 5. In other embodiments, the body 102 of phantom 100 may itself constitute a box and a pattern of opaque and translucent regions may be provided in a sheet, veneer, layer or the like surrounding chamber 104.

Phantom 100 has alignment markings 128 on its outer surface. In the illustrated embodiment, alignment markings 128 include lines 128A, 128B and 128C which lie in mutually perpendicular planes having known locations and orientations relative to chamber 104. Lines 128 can be used to align phantom 100 in the treatment area of a linear accelerator or other radiation source. If phantom 100 has a known location and orientation relative to the radiation source then the position of each sheet 111 relative to the radiation source can be determined from the positions of fiducial marks 112 since fiducial marks 112 indicate the location of each sheet 111 of film relative to phantom 100.

Phantom 100 may be constructed in a manner which permits relocating chamber 104 within body 102. In one construction, the interior of body 102 is filled with blocks of tissue-equivalent material. The location of cavity 104 can be changed by rearranging the blocks of tissue-equivalent material. The blocks are preferably tightly fitted together.

EXAMPLE

To ensure the validity of the recorded dose, it is crucial that the introduction of radiographic film into the anthropomorphic head phantom does not destroy the tissue equivalence of the phantom in terms of the deposition of dose by the photon beam. This question of tissue equivalence was examined by accurately modelling the phantom using a computer technique called Monte Carlo simulation. This simulation has been established over the years as the most accurate technique for dose calculation. Electron Gamma Shower 4 (EGS4) Monte Carlo simulations have been used to model seventeen adjacent films separated by 1/8" (approximately 3.2 mm) polystyrene spacers. Results of the simulation indicate that presence of the film in the phantom perturbs the deposited dose by less than 1% (compared to the dose deposited within a homogeneous polystyrene phantom without film). This is acceptable in order to guarantee that the dose recorded in the vicinity of the film is sufficiently close to that which would be present without the film.

A series of experiments was conducted to investigate possible dependencies of film sensitivity on field size, depth in a phantom, and film orientation. It has been shown that, for the range of field sizes used in radiosurgery, no significant dependencies exist. Therefore, only a single calibration curve is required to convert the film's optical density to dose.

Also, reproducibility studies have indicated that the production and subsequent measurement of film optical density are reproducible to within, on average, less than 2% between films within one processing session, and to within less than 3% between separate sessions.

While the preferred embodiments of the invention have been illustrated and described, it will be appreciated that various changes can be made therein without departing from the spirit and scope of the invention.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A film phantom system for recording and verifying three-dimensional dose distributions, the film phantom system comprising:
   a body of tissue-equivalent material, the body surrounding a cavity capable of receiving a stack of sheets of film separated by tissue-equivalent spacers;
   the cavity having walls, the walls including at least one translucent area which extends through at least one opaque area of the walls, the at least one translucent area configured to intersect edges of different sheets of film in a stack of sheets of film in the chamber at different locations.

2. A film phantom system according to claim 1 wherein the cavity is rectilinear.

3. A film phantom system according to claim 2 wherein the at least one translucent area comprises at least one translucent strip.

4. A film phantom system according to claim 3 wherein the at least one translucent strip comprises a first translucent strip extending across a first face of the chamber parallel to an edge of the face.

5. A film phantom system according to claim 4 wherein the at least one translucent strip comprises a second translucent strip extending across the first face of the chamber at an angle to the first translucent strip.

6. A film phantom system according to claim 5 wherein the at least one translucent strip comprises a third translucent strip extending across a second face of the chamber adjoining the first face of the chamber, the third translucent strip parallel to the first translucent strip.

7. A film phantom system according to claim 1 wherein the at least one translucent area comprises at least one translucent strip.

8. A film phantom system according to claim 1 wherein the body is cylindrical.

9. A film phantom system according to claim 1 wherein the body comprises a plurality of pieces of a solid tissue equivalent material and a location of the chamber within the body can be changed by rearranging the pieces of solid tissue-equivalent material.

10. A film phantom system according to claim 1 wherein the body comprises a fluid-filled shell and the cavity is defined within a box located within the fluid-filled shell.

11. A film phantom system according to claim 1 wherein the body has the shape of a human head.

12. A film phantom system according to claim 1 comprising a simulated lesion replaceably positionable within the cavity.

13. A film phantom system according to claim 1 comprising multiple layers of film in the cavity and separated from one another by multiple tissue-equivalent spacers.

14. A method of recording and verifying three-dimensional dose distributions, the method comprising:
provding a phantom including a tissue equivalent body surrounding a cavity;
loading multiple layers of film separated by multiple spacers having tissue-equivalent characteristics into the cavity;
delivering radiation to the body including the multiple layers of film;
before, during or after delivering the radiation to the body, allowing light to pass through translucent areas in walls of the cavity to expose a pattern of fiducial marks on edges of the multiple layers of film, the pattern being different for each of the multiple layers of film;
removing the multiple layers of film from the cavity;
obtaining multiple dose images based on the multiple layers of film;
using the patterns of fiducial marks exposed on the edges of the multiple layers of film to arrange the multiple dose images in sequence.

15. A method according to claim 14 comprising using the patterns of fiducial marks exposed on the edges of the multiple layers of film to orient the dose images.

16. A method according to claim 14 wherein exposing the pattern comprises exposing fiducial marks on at least two edges of each of the multiple layers of film.

17. A method according to claim 14 wherein exposing the pattern comprises exposing two fiducial marks on a first edge of each of the multiple layers of film, the two fiducial marks having a different spacing for each of the multiple layers of film.

18. A method according to claim 17 wherein exposing the pattern comprises exposing a third fiducial mark on a second edge of each of the multiple layers of film, the second edge adjacent to the first edge.

19. A method according to claim 14 comprising automatically ordering and orienting the multiple layers of film based upon the different pattern of fiducial marks on each of the multiple layers of film.

20. A method according to claim 14 comprising using the patterns of fiducial marks exposed on the edges of the multiple layers of film to determine a position of each of the sheets of film in a direction substantially perpendicular to the sheets of film.

21. A method according to claim 20 comprising using the patterns of fiducial marks exposed on the edges of the multiple layers of film to determine a position of each of the sheets of film in a plane of the sheet of film.

22. A method according to claim 14 comprising using the patterns of fiducial marks exposed on the edges of the multiple layers of film to determine a position of each of the sheets of film in each of two directions in a plane of the sheet of film.

23. A method according to claim 14 wherein delivering radiation to the body is performed when the body is in a known location relative to a source of the radiation and the method comprises determining locations of the sheets of film relative to the source of the radiation.

24. A method according to claim 23 wherein the source of radiation is a linear accelerator.

* * * * *